United States Patent
Van Wyk (10) Patent No.: US 10,398,468 B2
(45) Date of Patent: Sep. 3, 2019

(54) CIRCUMCISION AID

(71) Applicant: CIRCUMQ IP (RF) (PTY) LTD., Cape Town (ZA)

(72) Inventor: Hendrik Jakobus Van Wyk, Cape Town (ZA)

(73) Assignee: CIRCUMQ IP (RF) (PTY) LTD, Cape Town, Western Cape Province (ZA)

( * ) Notice: Subject to any disclaimer, the term of this patent is extended or adjusted under 35 U.S.C. 154(b) by 339 days.

(21) Appl. No.: 15/302,605

(22) PCT Filed: Apr. 9, 2015

(86) PCT No.: PCT/IB2015/052582
§ 371 (c)(1),
(2) Date: Oct. 7, 2016

(87) PCT Pub. No.: WO2015/155724
PCT Pub. Date: Oct. 15, 2015

(65) Prior Publication Data
US 2017/0119422 A1    May 4, 2017

(30) Foreign Application Priority Data
Apr. 9, 2014    (ZA) .................................. 2014/2562

(51) Int. Cl.
*A61B 17/326*    (2006.01)
(52) U.S. Cl.
CPC .................................. *A61B 17/326* (2013.01)

(58) Field of Classification Search
CPC .................................................... A61B 17/326
USPC ........................................................... 606/118
See application file for complete search history.

(56) References Cited

U.S. PATENT DOCUMENTS

| 5,163,943 A | 11/1992 | Mohiuddin et al. |
| 5,829,902 A * | 11/1998 | Fomby ................. A46B 11/001 401/127 |
| 2011/0178528 A1* | 7/2011 | Kostrzewski ........ A61B 17/326 606/118 |

FOREIGN PATENT DOCUMENTS

| CN | 103 536 342 | 1/2014 | |
| WO | 2002 060 329 | 8/2002 | |
| WO | 2007 145 595 | 12/2007 | |
| WO | 2009 091 235 | 7/2009 | |
| WO | WO-2009091235 A2 * | 7/2009 | .......... A61B 17/326 |
| WO | 2014 094 005 | 6/2014 | |

* cited by examiner

*Primary Examiner* — Martin T Ton
(74) *Attorney, Agent, or Firm* — Emerson Thomson Bennett, LLC; Daniel A. Thomson (57) ABSTRACT

The invention describes a single circumcision aid which limits circumcision scar formation and facilitates a fast healing time period. The circumcision aid includes a tubular section having a glans penis locating portion at a first open end region thereof, an opposite second end region and a body therebetween, the body including a threaded portion being received by a screw means. The circumcision aid also includes a framework providing stability to the aid, a crush means and a locking means.

14 Claims, 4 Drawing Sheets

CIRCUMCISION AID

FIELD OF INVENTION

This invention relates to a circumcision aid, more particularly to a single use circumcision aid.

BACKGROUND

Circumcision aids aimed at limiting possible damage to a penis of a male patient are well known. Typically, such aids provide a means to limit possible injury to the glans penis of said patient. Well known examples of such clamps include the mogen-type clamp, the gomco and the plastibel.

The mogen-type clamp in use clamps the prepuce whilst shielding the glans penis prior to removal of the prepuce using a scalpel blade. A known disadvantage of the mogen-type clamp is that a portion of the glans penis may also be clamped together with the prepuce resulting in eventual damage to the glans penis and/or urethra when the prepuce is removed. Careful use is needed to ensure no damage occurs to the glans penis and/or urethra of the patient. Apart from the dangers associated with use of mogen-type clamp, it is disadvantageous for use in rural settings where evacuation of an injured patient to a hospital with appropriate facilities may take several hours.

The use of Mogen® and mogen-type clamps inappropriately sized for patients has led to patient injuries. In such cases, the clamp may allow too much prepuce tissue to be drawn through an opening of the aid, thus facilitating the removal of an excessive amount of foreskin and in some cases, a portion of the glans penis.

The gomco clamp was designed to further provide protection means to the glans penis during circumcision procedures. Essentially, it is provided with a cone having an inner surface which receives the glans penis in use and the outer surface thereof being covered with the prepuce of the patient. The glans penis is therefore protected from injury when the prepuce is removed using a scalpel blade. Use of the gomco clamp is known to often cause cosmetically dissatisfactory results, and the procedure is complicated by the doctor/surgeon needing to carefully select the correct size of the so-called gomco bell for different patients. Further, the doctor/surgeon needs to decide for each patient what portion the prepuce to draw through a hole in a base plate of the gomco aid prior to surgically removing said portion of the prepuce. Incorrect assessment of what portion to remove could result in surgical complications and/or cosmetically dissatisfactory results.

The plastibell is not typically suited for adult male circumcision and is known to result in complications which may be severe enough to result in amputation of the penis.

Circumcision devices, circumcision surgical techniques and/or circumcision aids known in the art are associated with uneven scar formation, large scars forming after surgery, injury to the penis and/or an unaesthetic circumcised penis. Large and/or uneven scar formation may result with the penis adopting an undesired shape as healing takes place. Injury to the penis may include injury to the glans penis and/or the shaft and is known to result in sepsis and even amputation.

Circumcision is often ritual and/or part of traditional custom and practice of various population groups around the world. Such ritual circumcisions often take place in remote areas far from advanced medical health care.

HIV/AIDS and other diseases provides for a need to have circumcision aids being single use devices since multiple use devices might increase the risk of patients contracting HIV/AIDS.

There exists a need for a circumcision aid that will facilitate safe circumcision limiting penile injury and providing for even and/or limited scar formation, and after healing providing for an aesthetically pleasing circumcised penis.

SUMMARY

In accordance with this invention there is provided a circumcision aid comprising:
  a tubular section having a glans penis locating portion at a first open end region thereof, an opposite second end region and a body therebetween, the body including a threaded portion;
  a screw means for receiving therein the second end region and at least a section of the threaded portion;
  a framework including a base plate and a crush plate spaced apart from each other, each of the base plate and crush plate defining therein a first and second aperture respectively, for receiving therethrough the tubular section;
  a crush means including a circumferential rim extending inwardly toward a center of the second aperture and a portion of an outer surface of the glans penis location portion; and
  a locking means located along the body of the tubular section allowing axial displacement of the tubular section from a first glans penis locating position, wherein the glans penis is located inside the glans penis locating portion, the prepuce being located over the outer surface of the penis locating portion such that the circumferential rim and the portion of the outer surface defining the crush means are spaced apart, to a second locked prepuce crushing position, wherein the screw means can be manipulated to cause axial displacement of the tubular section such that the circumferential rim and the portion of the outer surface crush together a circumferential section of the prepuce.

In use, circumcision is commenced after the circumcision aid is in the locked prepuce crushing position. The crushed together circumferential section of the prepuce provides a guide together with the crush plate for a scalpel used to complete surgical removal of the prepuce from the penis in so doing resulting in even scar formation, faster healing of the resulting wound, and a more aesthetically circumcised penis. At all times during the circumcision the glans penis is protected by being received inside the glans penis locating portion. The locking means provides for a single use circumcision aid therein limiting the risk of a patient contracting HIV/AIDS.

The glans penis locating portion may be a hollow member having at least a first diameter substantially proximal the first open end region and a second diameter substantially distal the first open end region, wherein the first diameter is larger relative to the second diameter. The glans penis locating portion may preferably be a hollow member having a diameter that narrows as the hollow member extends away from the first open end region. Typically, the glans penis locating portion may be a conical hollow member. Further preferably, the glans penis locating portion may be a frusto conical shaped hollow member.

The portion of the outer surface of the glans penis locating portion may be a circumferential edge extending outwardly away from a terminating edge of the first end region.

The circumcision aid may further include a guide means for facilitating the axial displacement of the tubular section between the first glans penis locating position and the second locked prepuce crushing position. The guide means may comprise a pair of oppositely located indentations extending outwardly away from the first aperture and a pair of complementarily shaped protrusions located on opposite sides of the body of the tubular section, said protrusions extending outwardly away from opposite sides of the body of the tubular section.

The guide means facilitates the axial displacement of the tubular section between the first glans penis locating position and the second locked prepuce crushing position. The guide means may further prevent the tubular section from turning and/or rotating when the screw means is actuated to move the circumcision aid from the first glans locating position to the second locked prepuce crushing position, therein limiting injury to the penis and/or ensuring an even circumferential circumcision wound and scar.

The guide means also facilitates, in use, a substantially equal distribution of force exerted onto the crushed circumferential section of the prepuce when the circumcision aid is in the locked prepuce crushing position. The Applicant has surprisingly found that such substantially equal distribution of force exerted onto the crushed circumferential section of the prepuce facilitates even scar formation after circumcision therein providing for a more aesthetically circumcised penis. Further, the equal distribution of force exerted onto the crushed circumferential section of the prepuce provides for shorter healing periods after circumcision when compared to use of circumcision aids known in the art, particularly since the scar area is substantially minimized.

The framework may further comprise a pair of oppositely located pillar sections spacing apart the base plate from the crush plate.

The pair of oppositely located pillar sections may provide stability to the framework.

The pair of oppositely located pillar sections also facilitates, in use, a substantially equal distribution of force exerted onto the crushed circumferential section of the prepuce when the circumcision aid is in the locked prepuce crushing position. The Applicant has surprisingly found that such substantially equal distribution of force exerted onto the crushed circumferential section of the prepuce facilitates even scar formation after circumcision therein providing for a more aesthetically circumcised penis.

At least one of the pair of pillar sections may be removable from at least the base plate and/or the crush plate. Removing at least one pillar from the base plate may typically be actioned via a dual purpose removing-securing means.

The dual purpose removing-securing means may comprise a clip defining a securing zone and an unsecuring zone. The clip may include a handle portion and a pair of arms being a first and second arm. The pair of arms may define a securing zone distal the handle portion between the first and second arm, and an unsecuring zone proximal the handle portion between the first and second arm, wherein a space defined between the first and second arm is smaller in the securing zone relative to the unsecuring zone, the removing-securing means typically engaging the at least one pillar section and movable between a secured position, wherein the securing zone substantially surrounds the pillar, and an unsecured position, wherein the unsecured zone substantially surrounds the pillar section.

In use, the securing zone is positioned around a pillar to secure the pillar for use during circumcision. After circumcision the clip is manipulated such that the unsecuring zone substantially surrounds the pillar to allow removable of the pillar from the base plate and/or the crush plate. When in the securing zone stability of the circumcision aid is increased in use. The Applicant has surprisingly found that such substantially equal distribution of force exerted onto the crushed circumferential section of the prepuce, when the circumcision aid is in use, facilitates even scar formation after circumcision therein providing for a more aesthetically circumcised penis. Further, the equal distribution of force exerted onto the crushed circumferential section of the prepuce provides for shorter healing periods after circumcision when compared to use of circumcision aids known in the art, particularly since the scar area is substantially minimized.

The circumcision aid may further comprise a securing device comprising a pair of ribs extending inwardly away from the pair of arms and a pair of grooves located at a lower section of at least one pillar, such that in use, when the clip is in the secured position around the pillar the ribs matingly engage the grooves preventing displacement of the pillar away from the base plate. The securing device facilitates increasing stability of the circumcision aid in use.

The locking means may comprise a wedged member defining a sloping surface and a back wall, the back wall facing the first open end region of the tubular section, such that when the circumcision aid is in the first glans penis locating position the wedged member is located adjacent an upper face of the base plate and when the circumcision aid is in the second locked prepuce crushing position the wedged member is located adjacent a lower face of the base plate. Should a user attempt manipulation of the circumcision aid from the second locked position back to the first penis locating position the back wall of the wedged member will operatively abut against the lower face preventing movement back to the first glans penis locating position. This provides for the circumcision aid to be a single use aid. Multiple use circumcision aids increase the risk of spreading blood transmittable diseases such as HIV/AIDS.

The wedged member may be movable between a travel position, wherein the wedged member is movably receivable into a recess defined in the body of the tubular section, and a biased position wherein the wedged member extends outwardly away from the recess.

The screw means may further comprise a pair of oppositely located handles to facilitate screwing action by a user when the circumcision aid is in use.

The tubular section may further comprise a collar surrounding a part of the body of the tubular member located between the locking means, preferably the wedged member, and the first open end, the collar having a larger diameter relative to the first aperture of the base plate, such that in use, when the circumcision aid is in the second locked prepuce crushing position the collar prevents further displacement of the tubular member toward the screw means by operatively abutting against the upper surface of the base plate.

There is further provided for a circumcision aid substantially as herein described, illustrated and/or exemplified with reference to the accompanying diagrammatic figures.

According to a further aspect of the invention there is provided for a method of conducting a circumcision using the circumcision aid according to the invention, the method comprising:

receiving into the glans penis locating portion of the circumcision aid a glans penis of a human penis;

placement of a prepuce of the located glans penis over the outer surface of the penis locating portion;

screwing the screw means such that the circumcision aid moves from a first glans penis locating position, wherein the circumferential rim and the portion of the outer surface defining the crush means are spaced apart, to a second locked prepuce crushing position, wherein the screw means is manipulated to cause axial displacement of the tubular section such that the circumferential rim and the portion of the outer surface crush together a circumferential section of the prepuce;

cutting the prepuce substantially adjacent the crushed circumferential section of the prepuce, therein separating the prepuce from the penis;

manipulating the clip of the circumcision aid such that the unsecuring zone substantially surrounds the pillar to allow removable of the pillar from the base plate; and removing the tubular section of the circumcision aid from the circumcised glans penis.

A method of conducting a circumcision substantially as herein described, illustrated and/or exemplified with reference to the accompanying diagrammatic drawings.

BRIEF DESCRIPTION OF THE DRAWINGS

Embodiments of the invention will be described below by way of example only and with reference to the accompanying drawings in which.

DETAILED DESCRIPTION OF THE DRAWINGS

Figure 1:
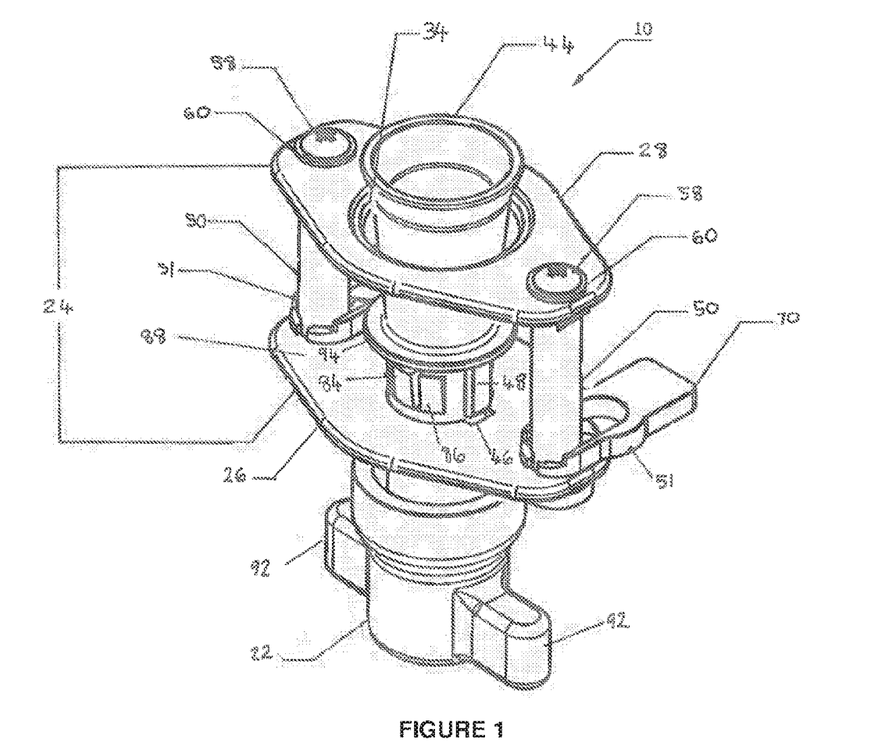
FIG. 1 shows a three dimensional view of a circumcision aid in a first glans penis locating position according to an embodiment of the invention.

Referring to the accompanying diagrammatic drawings FIG. 1 shows a circumcision aid and/or device 10 in accordance with the invention. The circumcision aid and/or device 10 comprises a tubular section 12 having a glans penis locating portion at a first open end region 14 thereof, an opposite second end region 16 and a body 18 therebetween, the body 18 including a threaded portion 20. The aid and/or device 10 further comprises a screw means 22 for receiving therein the second end region 16 and at least a section of the threaded portion 20, and a framework 24 including a base plate 26 and a crush plate 28 spaced apart from each other, each of the base plate 26 and crush plate 28 defining therein a first and second aperture 30, 32 respectively, for receiving therethrough the tubular section 12.

The circumcision aid and/or device 10 further comprises a crush means including a circumferential rim 34 extending inwardly toward a center of the second aperture 32 and a portion 36 of an outer surface 38 of the glans penis location portion 14.

The aid and/or device 10 further includes a locking means located along the body 18 of the tubular section 12 allowing axial displacement of the tubular section 12 from a first glans penis locating position (shown in FIG. 1), wherein the glans penis (not shown) is located inside the glans penis locating portion 14, the prepuce being located over the outer surface 38 of the penis locating portion 14 such that the circumferential rim 34 and the portion 36 of the outer surface 38 defining the crush means are spaced apart, to a second locked prepuce crushing position (shown in FIG. 2), wherein the screw means 22 can be manipulated to cause axial displacement of the tubular section 12 such that the circumferential rim 34 and the portion 36 of the outer surface 38 crush together a circumferential section of the prepuce (not shown). The prepuce is typically folded over the outer surface 38.

Figure 2:
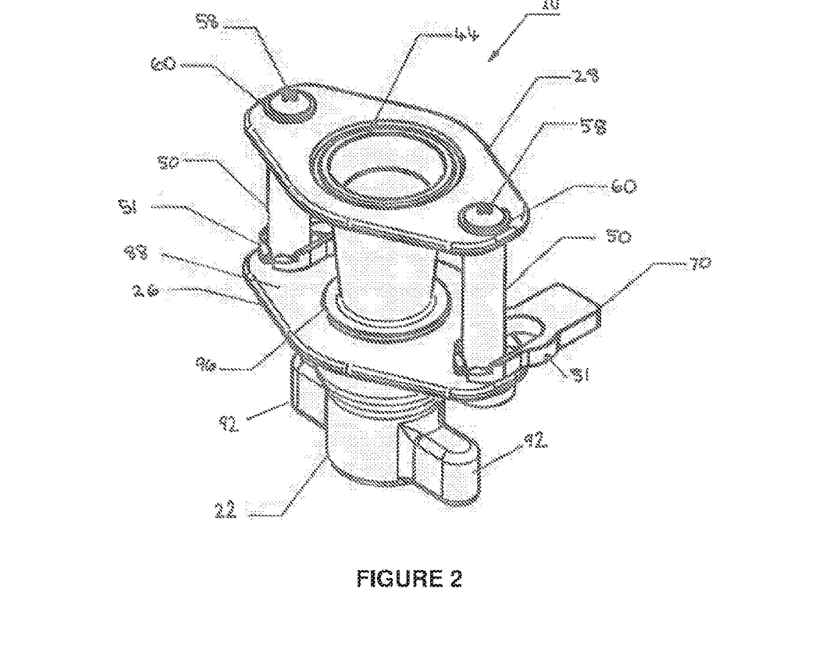
FIG. 2 shows a three dimensional view of the circumcision aid shown in FIG. 1 in a second prepuce crushing position according to an embodiment of the invention.

In use, circumcision is commenced after the circumcision aid 10 is in the locked prepuce crushing position (as shown in FIG. 2). The crushed together circumferential section of the prepuce provides a guide together with the crush plate 28 for a scalpel used to complete surgical removal of the prepuce from the penis in so doing resulting in even scar formation, faster healing of the resulting wound, and a more aesthetically circumcised penis. At all times during the circumcision the glans penis is protected by being received inside the glans penis locating portion 14 therein hindering injury to the glans penis and/or shaft. The locking means provides for a single use circumcision aid therein limiting the risk of a patient contracting HIV/AIDS. It will be understood that the amount of prepuce and/or mucosa selected for removal is adjustable and that it is this selected amount of prepuce that is removable. It will further be understood that circumcision using the aid according to the invention provides for shorter operating times compared to prior art devices and/or techniques.

The glans penis locating portion 14 is typically a hollow member having at least a first diameter 40 substantially proximal the first open end region and a second diameter 42 substantially distal the first open end region, wherein the first diameter is larger relative to the second diameter. The glans penis locating portion 14 is preferably a hollow member having a diameter that narrows as the hollow member extends away from the first open end region. In other words, the glans penis locating portion 14 tapers as it extends away from the first open end region. As shown in the FIGS. 1-3, the glans penis locating portion 14 is a conical hollow member. The glans penis locating portion may be a frusto conical shaped hollow member. In a further embodiment of the invention the glans penis locating portion may be bell shaped.

Figure 3:
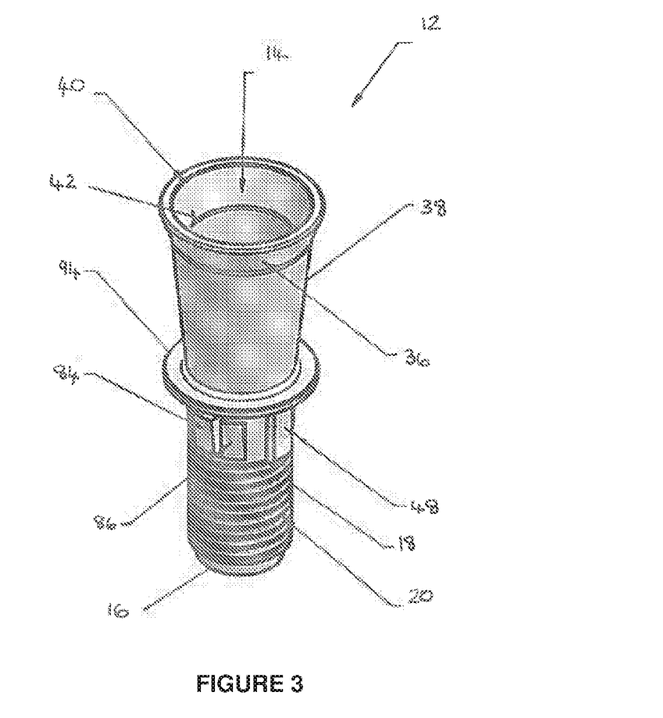
FIG. 3 shows a three dimensional view of a tubular section of the circumcision aid.
Figure 4:
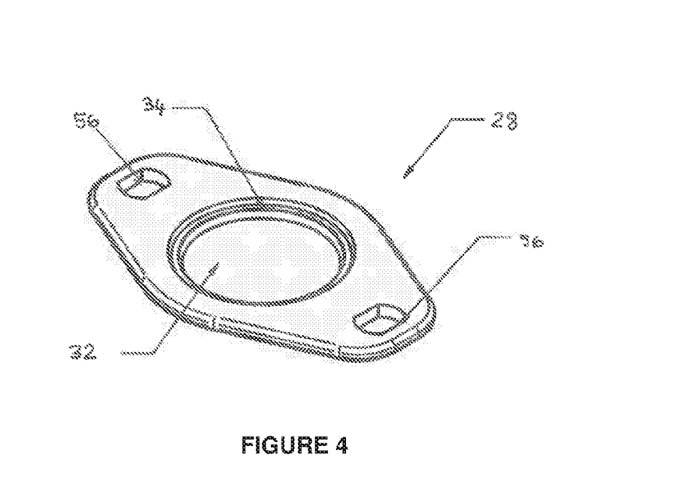
FIG. 4 shows a three dimensional view of a crushing plate of the circumcision aid.
Figure 5:
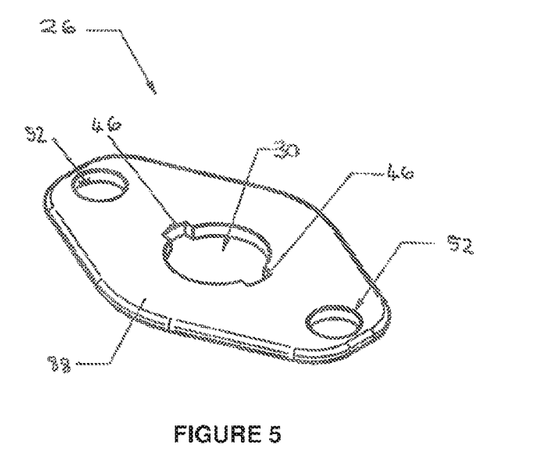
FIG. 5 shows a three dimensional view of a base plate of the circumcision aid.
Figure 6:
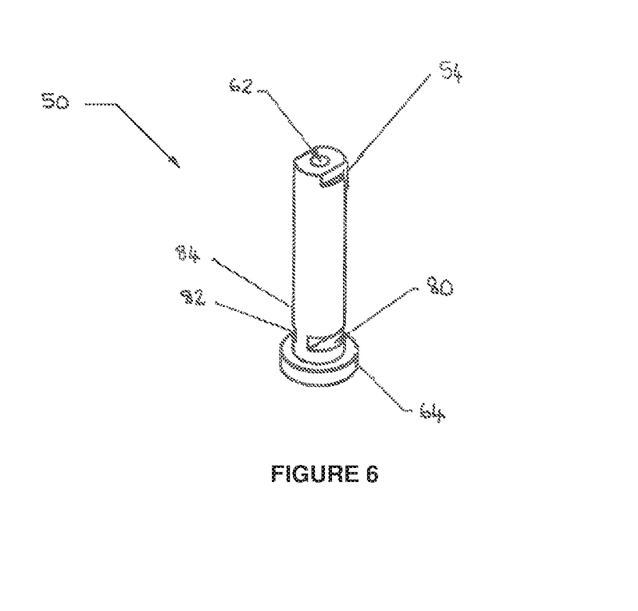
FIG. 6 shows a three dimensional view of a pillar section forming part of a pair of pillar sections spacing apart the crushing plate and the base plate.

The portion 36 of the outer surface 38 of the glans penis locating portion 14 is preferably a circumferential edge 44 extending outwardly away from a terminating edge of the first end region 14. It is to be understood that the portion 36 may be any portion of the outer surface 38 of the glans penis locating portion. Preferably, the portion 36 of the outer surface 38 is an area proximal the terminating edge as shown in FIG. 3. Owing to the tapering of the glans penis locating portion 14 a different portion located along any length of the outer surface 38, preferably the area proximal the terminating edge, may form the crush means, and typically differs depending on the thickness of the prepuce of the penis undergoing circumcision. The circumcision aid according to the invention has been specifically designed to allow for easy use across all ages (infants, minors and adults) and race groups, but caters for the generally thicker prepuce of the African patient. It is to be understood that the circumcision aid 10 may be manufactured in different sizes such that for example the diameter of the tubular section 12 may vary at its widest and narrowest areas. Typically the different sizes are manufactured to allow for different ages of patients. In a certain embodiment of the invention the circumferential rim 34 and/or the circumferential edge 44 may comprise a blade and/or a sharp edge.

The circumcision aid 10 may further include a guide means for facilitating the axial displacement of the tubular section between the first glans penis locating position (shown in FIG. 1) and the second locked prepuce crushing position (shown in FIG. 2). The guide means comprises a pair of oppositely located indentations 46 extending outwardly away from the first aperture 30 and a pair of complementarily shaped protrusions 48 located on opposite sides of the body 18 of the tubular section 12, said protrusions 48 extending outwardly away from opposite sides of the body of the tubular section 12. As best shown in FIGS. 1 and 3 the protrusions 48 are generally rectangular in shape having a length co-axial with the tubular section 12.

The guide means facilitates the axial displacement of the tubular section 12 between the first glans penis locating position (as shown in FIG. 1) and the second locked prepuce crushing position (as shown in FIG. 2).

The guide means also facilitates, in use, a substantially equal distribution of force exerted onto the crushed circumferential section of the prepuce when the circumcision aid is in the locked prepuce crushing position. An equal distribution of force exerted onto the crushed circumferential section of the prepuce provides for haemostasis preventing blood flow to the distal end portion of the crushed prepuce. The Applicant has surprisingly found that such substantially equal distribution of force exerted onto the crushed circumferential section of the prepuce facilitates even scar formation after circumcision therein providing for a more aesthetically circumcised penis. Further, the equal distribution of force exerted onto the crushed circumferential section of the prepuce provides for shorter healing periods after circumcision when compared to use of circumcision aids known in the art, particularly since the scar area is substantially minimized.

The guide means in use also prevents the tubular section 12 from turning and/or rotating when the screw means 22 is actuated to move the circumcision aid from the first glans locating position (as shown in FIG. 1) to the second locked prepuce crushing position (as shown in FIG. 2) therein limiting injury to the penis and/or ensuring an even circumferential circumcision wound and scar. The guide means, in use, acts to prevent turning and/or rotation of the tubular section 12 around its primary longitudinal axis and enables the screw means 22 to screw onto the tubular section 12 allowing for axial displacement of the tubular section 12. Without the guide means the screw means 22 will rotate freely without actuating axial displacement of the tubular section 12.

The framework 24 further comprises a pair of oppositely located pillar sections 50 spacing apart the base plate 26 from the crush plate 28. The pair of oppositely located pillar sections 50 provides stability to the framework 24.

The pair of oppositely located pillar sections 50 also facilitates, in use, a substantially equal distribution of force exerted onto the crushed circumferential section of the prepuce when the circumcision aid is in the locked prepuce crushing position (as shown in FIG. 2). An equal distribution of force exerted onto the crushed circumferential section of the prepuce provides for haemostasis preventing blood flow to the distal end portion of the crushed prepuce. The Applicant has surprisingly found that such substantially equal distribution of force exerted onto the crushed circumferential section of the prepuce facilitates even scar formation after circumcision therein providing for a more aesthetically circumcised penis.

At least one of the pair of pillar sections 50, but preferably both, is/are removable from at least the base plate 26 and/or the crush plate 28. Removing at least one pillar 50 from the base plate 26 may typically be actioned via a dual purpose removing-securing means 51 shown in FIGS. 1, 2, 8 and 10 as a clip.

Figure 9:
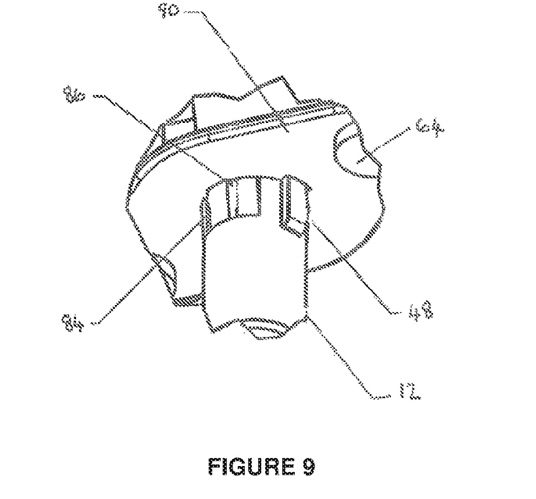
FIG. 9 shows a section of a lower face of a base plate, a guide means and a locking means of the circumcision aid.

Each of the pair of pillars 50 is inserted through an opening 52 of the base plate 26. It is understood that the top section 54, which is shaped to allow passage through the near rectangular openings 56 of the crush plate 28, of each pillar section 50 is inserted first through the opening 52 of the base plate 26 and is then pushed through openings 56 on the crush plate 28. By means of a screw 58 and washer 60 each pillar 50 is securely fastened. Each screw 58 engages an opening 62 defined at the flat top surface 54 of each pillar 50. A foot portion 64 of each pillar 50 is pushed until it operatively abuts the lower face 90 of the base plate 26 in use (as shown in FIG. 9).

Figure 8:
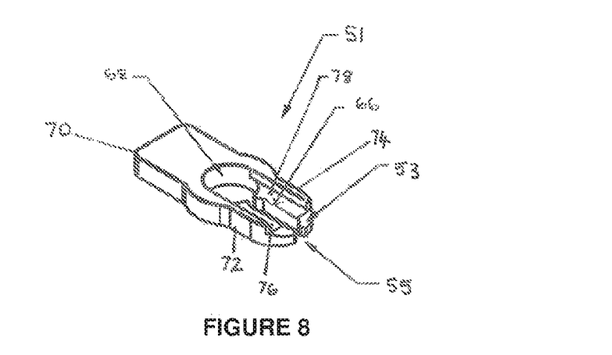
FIG. 8 shows a three dimensional view of a removing-securing means of the circumcision aid.

The dual purpose removing-securing means comprises a clip 51 defining a securing zone 66 and an unsecuring zone 68 as best illustrated on FIG. 8. The clip 51 includes a handle portion 70 and a pair of arms being a first and second arm 72, 74. The pair of arms 72, 74 may define a securing zone 66 distal the handle portion 70 between the first and second arm 72,74, and an unsecuring zone 68 proximal the handle portion 70 between the first and second arm 72,74, wherein a space defined between the first and second arm is smaller in the securing zone 66 relative to the unsecuring zone 68, the removing-securing means 51 typically engaging the at least one pillar section 51 and movable between a secured position (shown in FIGS. 1 and 2), wherein the securing zone 66 substantially surrounds the pillar 50, and an unsecured position (not shown), wherein the unsecured zone 68 substantially surrounds the pillar section 50. The pair of arms 72, 74 taper toward a substantially rounded front operative end 53 wherein a gap 55 is defined to provide guidance when inserting the clip 51 over a pillar section 50.

In use, the securing zone 66 is positioned around a pillar 50 to secure the pillar 50 for use during circumcision. After circumcision the clip 51 is manipulated such that the unsecuring zone 68 substantially surrounds the pillar 50 to allow removal of the pillar 50 from the base plate 26 and/or crush plate 28. When in the securing position (as shown in FIGS. 1 and 2) stability of the circumcision aid is increased in use. A substantially equal distribution of force exerted onto the crushed circumferential section of the prepuce when the circumcision aid is in the locked prepuce crushing position. The Applicant has surprisingly found that such substantially equal distribution of force exerted onto the crushed circumferential section of the prepuce, when the circumcision aid is in use, facilitates even scar formation after circumcision therein providing for a more aesthetically circumcised penis.

Further, the equal distribution of force exerted onto the crushed circumferential section of the prepuce provides for shorter healing periods after circumcision when compared to use of circumcision aids known in the art, particularly since the scar area is substantially minimized.

In the preferred embodiment of the invention illustrated in the figures, the circumcision aid 10 includes a pair of clips 51, one for each of the pair of pillar sections 50. In order to disassemble the circumcision aid 10 after use both clips 51 need to be disengaged from the pillar sections 50. Similarly, both clips 51 are needed to secure the pillar sections 50 to the base plate 26 prior to circumcision being conducted.

The circumcision aid further comprises a securing device comprising a pair of ribs 76,78 extending inwardly away from the pair of arms and a pair of grooves 80,82 located at a lower section 84 of at least one pillar 50, such that in use, when the clip 51 is in the secured position around the pillar 50 the ribs 76,78 matingly engage the grooves 80,82 preventing displacement of the pillar 50 away from the base plate 26 and/or crush plate 28. The securing device facilitates increasing stability of the circumcision aid in use. The clips 51 and their respective securing devices facilitate in providing a crush surface when the circumcision aid 10 is actuated from the first glans penis locating position (shown in FIG. 1) to the second locked prepuce crushing position (as shown in FIG. 2).

The locking means comprises a wedged member, and in FIGS. 1 and 9 two wedged members 84, 86, defining a sloping surface and a back wall, the back wall facing the first open end region 14 of the tubular section 12, such that when the circumcision aid is in the first glans penis locating position (as shown in FIG. 1) the wedged members 84,86 are located adjacent an upper face 88 of the base plate 26 and when the circumcision aid is in the second locked prepuce crushing position (as shown in FIG. 2) the wedged members 84,86 are located adjacent a lower face 90 of the base plate 26. Should a user attempt manipulation of the circumcision aid from the second locked position back to the first penis locating position the back wall of the wedged members will operatively abut against the lower face 90 preventing movement back to the first glans penis locating position. This provides for the circumcision aid to be a single use aid. Multiple use circumcision aids increase the risk of spreading blood transmittable diseases such as HIV/AIDS.

The wedged member may be movable between a travel position, wherein the wedged member is movably receivable into a recess defined in the body of the tubular section, and a biased position wherein the wedged member extends outwardly away from the recess. In the figures two types of different wedged members are shown, one type being movable 84 and the other type not being moveable 86. In the preferred embodiment of the invention illustrated in the figures the non-movable type 86 of wedged member provides for an extra mechanism to ensure a single use circumcision aid since there can be no manipulation to move the circumcision aid back from the second locked position to the first glans locating position.

Figure 7:
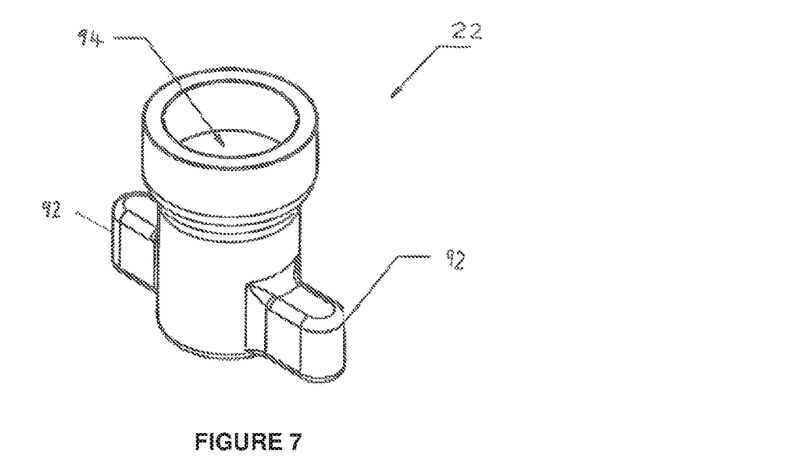
FIG. 7 shows a three dimensional view of a screw means of the circumcision aid.

The screw means 22 further comprises a pair of oppositely located handles 92 to facilitate screwing action by a user when the circumcision aid is in use, as shown in FIGS. 1, 2 and 7. The oppositely located handles 92 further facilitates an even distribution of force when in use. The screw means 22 has a complementarily shaped screw thread on its inside surface 94 to receive the screw thread 20 of the tubular section 12 in use.

When in use the screw means 22 is manipulated by the handles 92 to move the circumcision aid from the first glans penis locating position (as shown in FIG. 1) to the second locked prepuce crushing position (as shown in FIG. 2). The second locked prepuce crushing position is reached once the moveable wedged member 84 and non-movable wedged member 86 make an audible "click" sound indicating that the wedged members 84,86 are now proximal the lower face 90 of the base plate 26. Continued manipulation of the handles 92 will cause a collar 96 to abut against upper face 88 of the base plate 26. Counter manipulation of the handles 92 will cause the back walls of the wedged members 84,86 to operatively abut against the lower face 90 of the base plate 26 therein preventing movement back to the first glans penis locating position. This provides for a single use circumcision aid.

The tubular section 12 further comprises a collar 96 surrounding a part of the body 18 of the tubular member 12 located between the locking means, preferably the wedged members 84,86, and the first open end region 14, the collar 96 having a larger diameter relative to the first aperture 30 of the base plate 26, such that in use, when the circumcision aid is in the second locked prepuce crushing position (as shown in FIG. 2) the collar prevents 96 further displacement of the tubular member 12 toward the screw means 22 by operatively abutting against the upper surface 88 of the base plate 26. The collar 96 is best illustrated in FIGS. 1, 2 and 3.

The material of choice for the efficient working of the circumcision device 10 is chosen such that the device must be as light as possible without compromising any strength. The tubular section 12 should be made of a transparent material to allow visibility during the circumcision procedures. As such the tubular section 12 may comprise a plastics material, preferably a transparent plastics material. The crushing plate 28 and base plate 26 should be made from a strong rigid material that is rust free and strong under bending to accommodate any pressure that is applied to their surfaces. The material of the pillar sections 50 should be light weight and strong under buckling. The screwing means 22 should be light weight and should withstand tensile forces in an axial direction. The removable clip 51 section should be made out of a strong flexible material that will not fail under pressure but should be flexible allow the clip 51 to release when a pull, twist or push force is applied. The screw 58 and washer 60 should be made out of a rust free material.

There is further provided for a circumcision aid substantially as herein described, illustrated and/or exemplified with reference to the accompanying diagrammatic figures.

The invention extends to a method of conducting a circumcision utilizing the circumcision aid 10 according to the invention. Circumcision is commenced after the circumcision aid 10 is in the locked prepuce crushing position (as shown in FIG. 2). The crushed together circumferential section of the prepuce provides a guide together with the base plate for a scalpel used to complete surgical removal of the prepuce from the penis in so doing resulting in even scar formation, faster healing of the resulting wound, and a more aesthetically circumcised penis. At all times during the circumcision the glans penis is protected by being received inside the glans penis locating portion.

The circumcision aid in use allows for the crushing together a circumferential section of the prepuce prior to circumcision. The crushing together provides a thin crush line circumferential section and facilitates blocking of blood flow to the area of the prepuce extending away from the crush line. The blocking of blood flow facilitates substantially complete haemostasis in use. The thin crush line further facilitates a smaller wound relative to the use of circumcision aids known in the prior art and also facilitates a smaller scar. A smaller wound substantially reduces the risk of infection. The crush line provides for an even circumferential guide during circumcision and results in even scarring and an aesthetically circumcised penis. The thin crush line also facilitates accelerated post operative healing. Generally, a full recovery may be expected within 3 weeks after circumcision, or between 3-4 weeks after circumcision.

The circumcision aid 10 according to the invention provides for an easy to use circumcision aid, even by untrained medical professionals and/or inexperienced medical professionals limiting injury in use and preventing multiple use which is associated with the spread of disease. The method of circumcision utilizing the circumcision aid according to the invention provides for primary healing which is quicker relative to using prior art devices, creates less necrotic tissue, and leaves less chance for infection when compared to use of prior art devices.

Figure 10:
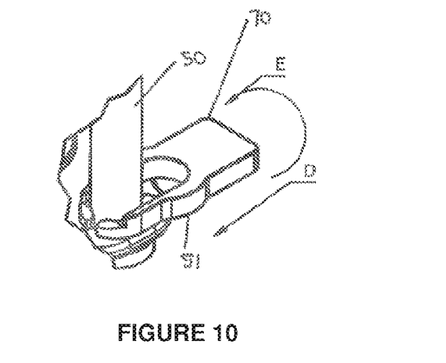
FIG. 10 shows the removing-securing means of the circumcision aid in use to remove and/or secure the pillar section.

Once circumcision has been conducted the circumcision aid should be removed from the penis. The clip 51 as shown in FIGS. 8 and 10 must now be removed. By pushing the clip 51 at the handle 70 in direction indicated by arrow D in FIG. 10 the unsecuring zone 68 is moved to substantially surround the pillar 50 in so doing unsecuring the pillar 50 from the base plate 26 and/or crush plate 28. Twisting the clip 51 in a counter clockwise direction indicated by arrow E in FIG. 10 will separate the clip 51 from the pillar 50. Now the pillar 50 can be easily removed from the base 26 and/or crush plate 28, and the glans penis removed from the inside of the glans penis locating portion. The penis can now be allowed to heal.

While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the claims and any equivalents thereto, which claims are appended hereto.

The invention claimed is:

1. A circumcision aid comprising:
a tubular section having a glans penis locating portion at a first open end region thereof, an opposite second end region and a body therebetween, the body including a threaded portion;
a screw means for receiving therein the second end region and at least a section of the threaded portion;
a framework including a base plate and a crush plate spaced apart from each other, each of the base plate and crush plate defining therein a first and second aperture respectively, for receiving therethrough the tubular section;
a crush means including a circumferential rim extending inwardly toward a center of the second aperture and a portion of an outer surface of the glans penis location portion;
a locking means located along the body of the tubular section allowing axial displacement of the tubular section from a first glans penis locating position, wherein, in use, a glans penis is arranged to be located inside the glans penis locating portion and a prepuce is arranged to be located over the outer surface of the glans penis locating portion such that the circumferential rim and the portion of the outer surface defining the crush means are spaced apart, to a second locked prepuce crushing position, wherein the screw means can be manipulated to cause axial displacement of the tubular section such that the circumferential rim and the portion of the outer surface crush together a circumferential section of the prepuce; and
a guide means for facilitating the axial displacement of the tubular section between the first glans penis locating position and the second locked prepuce crushing position, wherein the guide means comprises a pair of oppositely located indentations extending outwardly away from the first aperture and a pair of complementarily shaped protrusions located on opposite sides of the body of the tubular section, said protrusions extending outwardly away from opposite sides of the body of the tubular section, wherein the locking means comprises a wedged member defining a sloping surface and a back wall, the back wall facing the first open end region of the tubular section, such that when the circumcision aid is in the first glans penis locating position the wedged member is located adjacent an upper face of the base plate and when the circumcision aid is in the second locked prepuce crushing position the wedged member is located adjacent a lower face of the base plate.

2. The circumcision aid according to claim 1, wherein the glans penis locating portion is a hollow member having at least a first diameter substantially proximal the first open end region and a second diameter substantially distal the first open end region, wherein the first diameter is larger relative to the second diameter.

3. The circumcision aid according to claim 2, wherein the hollow member has a diameter that narrows as the hollow member axially extends away from the first open end region, in so doing forming a conical hollow member.

4. The circumcision aid according to claim 1, wherein the portion of the outer surface of the glans penis locating portion is a circumferential edge extending outwardly away from a terminating edge of the first end region.

5. The circumcision aid according to claim 1, wherein the framework further comprises a pair of oppositely located pillar sections spacing apart the base plate from the crush plate.

6. The circumcision aid according to claim 5, further comprising a removing-securing means to, in use, remove and/or secure at least one of the pair of pillar sections from and/or to the base plate respectively.

7. The circumcision aid according to claim 6, wherein the removing-securing means comprises a clip having a handle portion and a pair of arms being a first and second arm, the pair of arms defining a securing zone distal the handle portion between the first and second arm, and an unsecuring zone proximal the handle portion between the first and second arm, wherein a space defined between the first and second arm is smaller in the securing zone relative to the unsecuring zone,
the removing-securing means engaging the at least one pillar section and movable between a secured position, wherein the securing zone substantially surrounds the pillar section, and an unsecured position, wherein the unsecured zone substantially surrounds the pillar section.

8. The circumcision aid according to claim 7, wherein the circumcision aid further comprises a securing device comprising a pair of ribs extending inwardly away from the pair of arms and a pair of grooves located at a lower section of at, least one pillar section, such that in use, when the clip is in the secured position around the pillar section, the ribs matingly engage the grooves preventing displacement of the pillar section away from the base plate.

9. The circumcision aid according to claim 1, wherein the wedged member is movable between a travel position, wherein the wedged member is movably received into a recess defined in the body of the tubular section, and a biased position wherein the wedged member extends outwardly away from the recess.

10. The circumcision aid according to claim 1, wherein the screw means further comprises a pair of oppositely located handles to facilitate screwing action by a user when the circumcision aid is in use.

11. The circumcision aid according to claim 1, wherein the tubular section further comprises a collar surrounding a part of the body of the tubular member located between the locking means and the first open end, the collar having a larger diameter relative to the first aperture of the base plate, such that in use, when the circumcision aid is in the second locked prepuce crushing position the collar prevents further displacement of the tubular member toward the screw means by operatively abutting against the upper surface of the base plate.

12. A circumcision aid comprising:
    a tubular section having a glans penis locating portion at a first open end region thereof, an opposite second end region and a body therebetween, the body including a threaded portion;
    a screw means for receiving therein the second end region and at least a section of the threaded portion;
    a framework including a base plate and a crush plate spaced apart from each other, each of the base plate and crush plate defining therein a first and second aperture respectively, for receiving therethrough the tubular section;
    a pair of oppositely located pillar sections spacing apart the base plate from the crush plate;
    a removing-securing means to, in use, remove and/or secure at least one of the pair of oppositely located pillar sections from and/or to the base plate respectively;
    a crush means including a circumferential rim extending inwardly toward a center of the second aperture and a portion of an outer surface of the glans penis location portion;
    a locking means located along the body of the tubular section allowing axial displacement of the tubular section from a first glans penis locating position, wherein, in use, a glans penis is arranged to be located inside the glans penis locating portion and a prepuce is arranged to be located over the outer surface of the glans penis locating portion such that the circumferential rim and the portion of the outer surface defining the crush means are spaced apart, to a second locked prepuce crushing position, wherein the screw means can be manipulated to cause axial displacement of the tubular section such that the circumferential rim and the portion of the outer surface crush together a circumferential section of the prepuce; and
    a guide means for facilitating the axial displacement of the tubular section between the first glans penis locating position and the second locked prepuce crushing position, wherein the guide means comprises a pair of oppositely located indentations extending outwardly away from the first aperture and a pair of complementarily shaped protrusions located on opposite sides of the body of the tubular section, said protrusions extending outwardly away from opposite sides of the body of the tubular section.

13. The circumcision aid according to claim 12, wherein the removing-securing means comprises a clip having a handle portion and a pair of arms being a first and second arm, the pair of arms defining a securing zone distal the handle portion between the first and second arm, and an unsecuring zone proximal the handle portion between the first and second arm, wherein a space defined between the first and second arm is smaller in the securing zone relative to the unsecuring zone,
    the removing-securing means engaging the at least one pillar section and movable between a secured position, wherein the securing zone substantially surrounds the pillar section, and an unsecured position, wherein the unsecured zone substantially surrounds the pillar section.

14. The circumcision aid according to claim 13, wherein the circumcision aid further comprises a securing device comprising a pair of ribs extending inwardly away from the pair of arms and a pair of grooves located at a lower section of at least one pillar section, such that in use, when the clip is in the secured position around the pillar section the ribs matingly engage the grooves preventing displacement of the pillar section away from the base plate.

\* \* \* \* \*